United States Patent
Hatch et al.

(10) Patent No.: US 10,801,961 B2
(45) Date of Patent: Oct. 13, 2020

(54) REAL-TIME MULTI-PARAMETER MONITOR FOR METAL-WORKING SYSTEMS

(71) Applicant: Ionic Superior Technologies, El Paso, TX (US)

(72) Inventors: Gerald Travis Hatch, El Paso, TX (US); Quintin Hatch, El Paso, TX (US); Caibin Xiao, Holliston, MA (US)

(73) Assignee: IONIC SUPERIOR TECHNOLOGIES, El Paso, TX (US)

( * ) Notice: Subject to any disclaimer, the term of this patent is extended or adjusted under 35 U.S.C. 154(b) by 36 days.

(21) Appl. No.: 15/968,705

(22) Filed: May 1, 2018

(65) Prior Publication Data
US 2018/0313755 A1    Nov. 1, 2018

Related U.S. Application Data

(60) Provisional application No. 62/492,860, filed on May 1, 2017.

(51) Int. Cl.
*G01N 27/416*    (2006.01)
*G01N 21/64*    (2006.01)
(Continued)

(52) U.S. Cl.
CPC ........... *G01N 21/643* (2013.01); *G01N 21/85* (2013.01); *G01N 27/4167* (2013.01);
(Continued)

(58) Field of Classification Search
CPC ............. G01N 21/643; G01N 27/4167; G01N 33/2888; G01N 27/4168;
(Continued)

(56) References Cited

U.S. PATENT DOCUMENTS

| 4,577,109 A | * | 3/1986 | Hirschfeld | ........... | G01N 21/255 |
| | | | | | 250/461.1 |
| 4,963,815 A | | 10/1990 | Hafeman | | |

(Continued)

FOREIGN PATENT DOCUMENTS

EP    0874234 A1    10/1998

OTHER PUBLICATIONS

International Search Report and Written Opinion, PCT/US2018/030543, dated Aug. 1, 2018, in 9 pages.

*Primary Examiner* — J. Christopher Ball
(74) *Attorney, Agent, or Firm* — Chang & Hale LLP

(57) ABSTRACT

Disclosed herein are systems and methods configured for real-time multi-parameter monitoring of fluid systems associated with metal-working equipment. The disclosed fluid monitoring systems are configured to acquire in real time multiple parameters associated with the well-being of fluid systems of metal-working equipment. The data acquired in real-time can also be provided to remote devices to allow off-site personnel to monitor metal-working equipment. The fluid monitoring systems can also include fluorescence probes configured to determine fluid concentration and/or soil load values using fluorescence. The fluorescence probes can provide excitation light and detect emission light forming a small angle with respect to one another, emission light coming from a surface of the metal-working fluid.

8 Claims, 10 Drawing Sheets

(51) Int. Cl.
    *G01N 33/28*     (2006.01)
    *G01N 21/85*     (2006.01)
    *G01N 21/41*     (2006.01)

(52) U.S. Cl.
    CPC ..... *G01N 27/4168* (2013.01); *G01N 33/2888* (2013.01); *G01N 33/2894* (2013.01); *G01N 21/4133* (2013.01); *G01N 27/4166* (2013.01); *G01N 2021/6419* (2013.01); *G01N 2021/6421* (2013.01); *G01N 2021/6439* (2013.01)

(58) Field of Classification Search
    CPC ... G01N 2021/6439; G01N 2021/6421; G01N 33/2894; G01N 21/85; G01N 21/4133; G01N 2021/6419; G01N 27/4166
    See application file for complete search history.

(56) References Cited

U.S. PATENT DOCUMENTS

| | | |
|---|---|---|
| 6,860,142 B2 | 3/2005 | Seevers et al. |
| 9,140,648 B2 | 9/2015 | Tokhtuev et al. |

\* cited by examiner

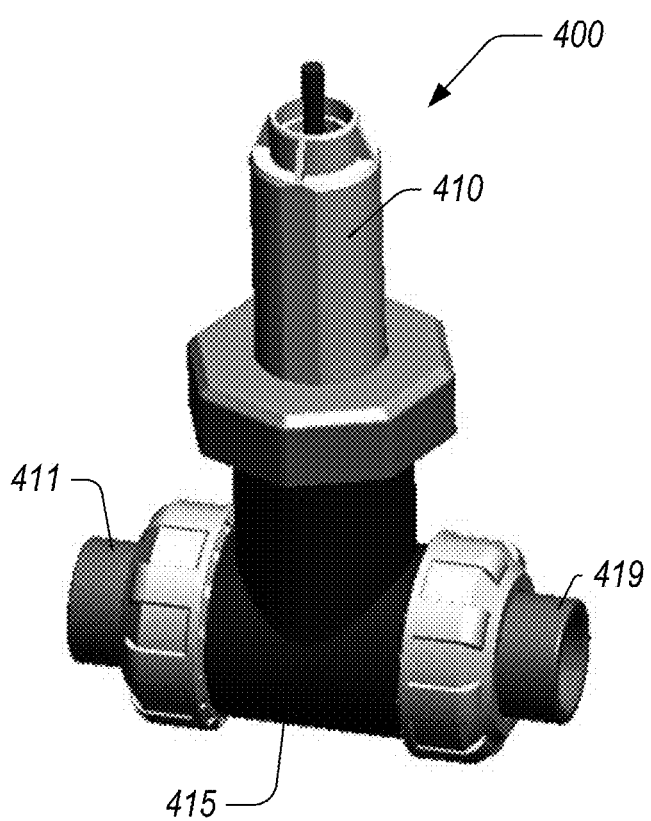
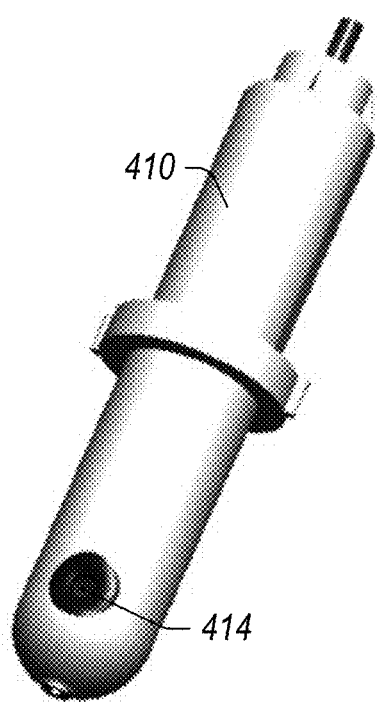
FIG. 4A
FIG. 4B

REAL-TIME MULTI-PARAMETER MONITOR FOR METAL-WORKING SYSTEMS

CROSS-REFERENCE TO RELATED APPLICATIONS

The present application claims priority to U.S. Provisional Application No. 62/492,860 entitled "REAL-TIME MULTI-PARAMETER MONITOR FOR MACHINING SYSTEMS" and filed May 1, 2017, the entire contents of which is incorporated by reference herein for all purposes.

This application is also related to U.S. patent application Ser. No. 15/487,169 entitled "MULTIPLE ASPECT MACHINING PROBE SYSTEM" filed Apr. 13, 2017, the entire contents of which is incorporated by reference herein for all purposes.

BACKGROUND

Field

The present disclosure generally relates to monitoring parameters of a fluid in metal-working systems, and in particular to real-time monitoring of multiple parameters of that fluid and to monitoring fluid concentration and/or soil load using inline fluorescence probes.

Description of Related Art

Metal-working fluids ("MWFs") are industrial coolants and lubricants used to reduce friction and heat generated during machining, grinding and fabrication operations of metal products and to lubricate various parts during metal-working operations. The fluids prolong the life of machines, carry away metal chips and protect the surfaces of the metal being processed. There are three main types of MWFs: insoluble fluids (straight or neat oils), soluble oils (oil in water emulsions) and synthetic fluids. These fluids can include additives such as corrosion inhibitors, emulsifiers, anti-foaming agents, preservatives and biocides. The formula used depends on the raw material or cutting operation to be carried out. Examples of the processes in which MWFs are used include can making, metal rolling, punching, sheet bending, and the like. Typically, the processes recirculate spent fluid from the metal-working process through a filtration and equilibration system to remove metal fines, tramp oil, soils, etc., and return the fluid to the metal-working process.

Typical metal-working equipment that remove metal, including computer controlled machining centers, rely upon such cooling and lubricating fluids applied to the machining site to improve tool life, to enhance the surface finish of the machined region, to increase cutting speeds, and to remove heat from the machining process that can reduce or minimize distortion of the part and can reduce or minimize interference with or reduction of properties achieved by heat treatment. Maintaining targeted concentrations and fluid characteristics of such cooling and lubricating fluids is desirable from the standpoints of maintaining desired machining conditions, improving or maximizing coolant and lubricant service life, and therefore reducing or minimizing overall operating expenses.

SUMMARY

According to a number of implementations, the present disclosure relates to a real-time, multi-parameter fluid monitoring system. The system includes a first probe comprising a pH sensor and an oxidation reduction potential sensor. The system also includes a second probe comprising fluid concentration sensor. The system also includes a supply line configured to extract a portion of a coolant from a sump and a return line configured to return the portion of the coolant to the sump. The system also includes a fluid monitoring apparatus configured to direct the portion of the coolant to the first probe and to the second probe, the fluid monitoring apparatus in fluid communication with the supply line and the return line. The system also includes a sensor data processor configured to receive measurements from the first probe and the second probe and to determine parameters associated with the respective sensors. The system also includes a server configured to receive the determine parameters from the sensor data processor, the server configured to provide the determined parameters to one or more remote devices over a network interface.

In some embodiments, the second probe further comprises a temperature sensor. In some embodiments, the fluid concentration sensor comprises a fluorescence probe. In further embodiments, the fluorescence probe is configured to direct excitation light to a surface of the coolant to measure emission light from the surface of the coolant. In further embodiments, the excitation light causes the coolant to fluoresce. In further embodiments, the excitation light causes a fluorescent tracer in the coolant to fluoresce.

In some embodiments, the second probe further comprises a soil load sensor. In further embodiments, the soil load sensor comprises a fluorescence probe. In further embodiments, the fluid concentration sensor comprises a first fluorescence probe and the soil load sensor comprises a second fluorescence probe. In further embodiments, the fluid concentration sensor is configured to detect a first color of emission light and the soil load sensor is configured to detect a second color of emission light different from the first color. In further embodiments, the fluid concentration sensor and the soil load sensor are housed within the same sensor housing.

According to a number of implementations, the present disclosure relates to a method of monitoring a concentration of a metal-working fluid. The method includes directing first excitation light having a first excitation color to a surface of the metal-working fluid. The method also includes measuring first fluorescent light having a first emission color emitted from the surface of the metal-working fluid, the first fluorescent light forming a small angle with respect to the first excitation light. The method also includes determining a concentration or a soil load of the metal-working fluid based on the measured first fluorescent light.

In some embodiments, the method further includes filtering the excitation light prior to the excitation light reaching the surface of the metal-working fluid. In further embodiments, the method further includes filtering the emission light prior to measuring the emission light.

In some embodiments, the method further includes directing a portion of a metal-working fluid from a reservoir to a flow-cell. In some embodiments, the method further includes automatically adjusting a property of the metal-working fluid in response to the determined concentration or soil load.

In some embodiments, the method further includes directing second excitation light having a second excitation color different from the first excitation color to the surface of the metal-working fluid; measuring second fluorescent light having a second emission color different from the first emission color emitted from the surface of the metal-working fluid, the second fluorescent light forming a small angle with respect to the second excitation light; determining the concentration of the metal-working fluid based on the measured first fluorescent light; and determining the soil load of the metal-working fluid based on the measured second fluorescent light.

In some embodiments, the method further includes determining a pH level, a temperature, and an oxidation reduction potential of the metal-working fluid based at least in part on measurements from one or more sensors. In further embodiments, the method further includes transmitting the determined pH level, temperature, oxidation reduction potential, and fluid concentration or soil load to one or more remote devices. In further embodiments, the method further includes generating a real-time data visualization based on the transmitted pH level, temperature, oxidation reduction potential, and fluid concentration or soil load.

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

FIGS. 4A and 4B illustrate example fluorescence probes configured to determine concentrations of a fluid in a metal-working system.

DETAILED DESCRIPTION OF SOME EMBODIMENTS

Figure 1:
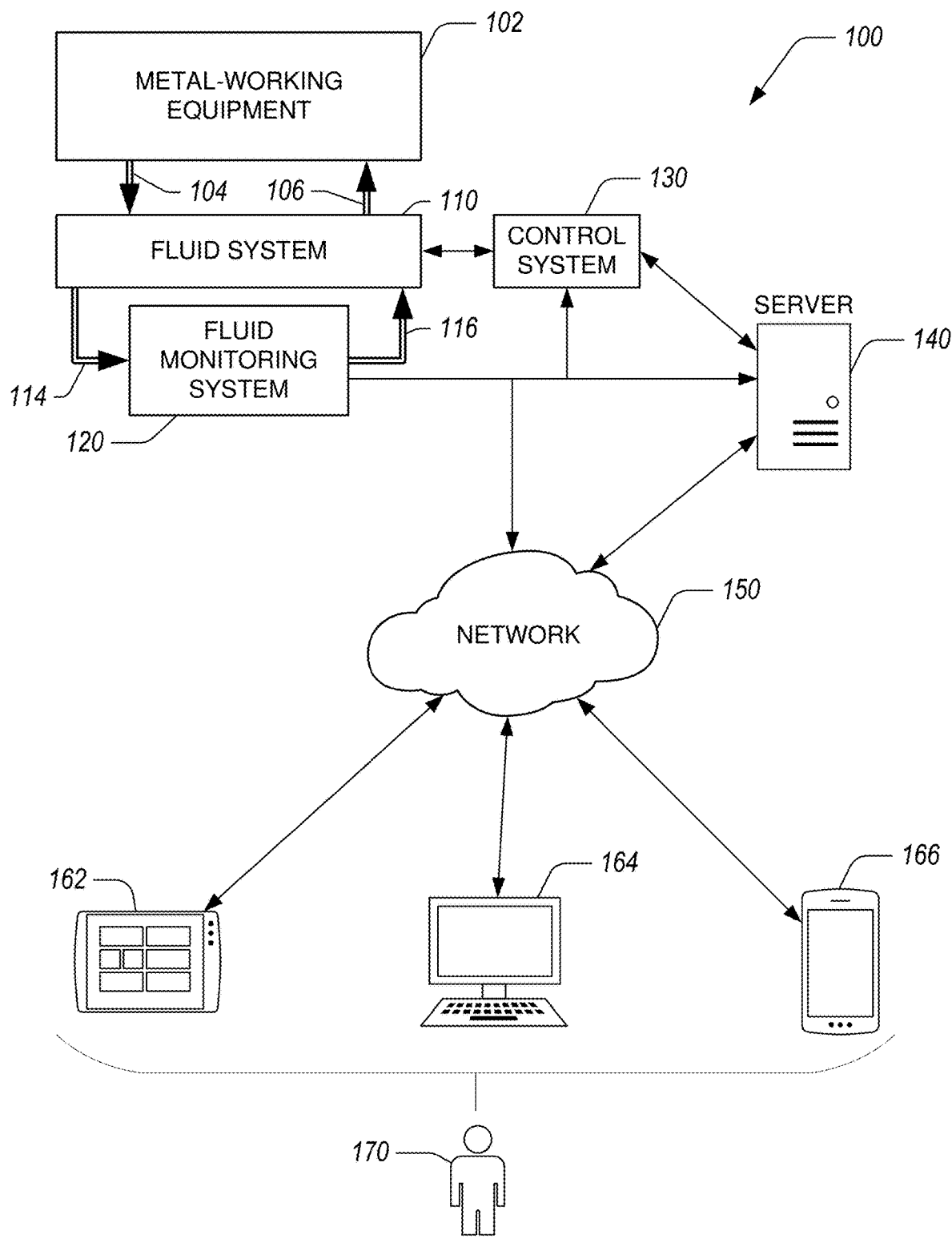
FIG. 1 illustrates a real-time, multi-parameter monitor for a fluid system for a metal-working system that provides data indicative of characteristics of the fluid to one or more remote devices in real time.

The headings provided herein, if any, are for convenience only and do not necessarily affect the scope or meaning of the claimed invention.

Overview

Described herein are fluid monitoring systems for metal-working systems (e.g., machining systems), the fluid monitoring systems configured to monitor multiple parameters simultaneously and in real-time. The real-time data can be provided to one or more remote devices to enable off-site personnel to monitor the health and well-being of metal-working systems and their fluids. The parameters can include pH, temperature, concentration, soil load, oxidation reduction potential (ORP), and the like. As used herein, the term "real-time" includes measurement, computation, storage, and/or delivery of fluidic parameters in less than or equal to 1 minute, less than or equal to 10 seconds, less than or equal to 5 seconds, or less than or equal to one second from acquisition of the corresponding data.

Described herein are fluorescence probes for fluid monitoring systems, the fluorescence probes configured to determine concentrations and/or soil loads in a fluid based at least in part on fluorescence signals. The fluorescence probes can be configured to be placed in a fluid channel, to emit excitation light, to measure emission light from the fluid, and to determine a fluid concentration and/or soil load based at least in part on the measured signals.

Improper control of chemical concentration in a metal-working fluid (e.g., a coolant) is a significant contributor to coolant-related machining problems. When concentrations of the active chemicals become too low, tool life is shortened and rust and corrosion begin to take place on the machine tools and on the manufactured parts. Surface finish is impaired and microbial and fungus growth begins to flourish. Similarly, when the metal-working fluids become too rich, tool life is again shortened due to impairment of heat dissipation caused by increased fluid viscosity. Maintenance of machinery becomes a problem because heavy, sticky residue begins to accumulate on machine surfaces and tool holders. Excessive chemical consumption and related costs become significant issues.

Controlling the quality or characteristics of metal-working fluids can significantly enhance the ability of the fluid to reduce friction heat by lubricating the cutting tool and work piece. Additionally, maintaining the fluid at a targeted concentration, pH, ORP, soil load, etc. can enhance its ability to dissipate heat that would otherwise build up on the tool as well as the work piece. Maintaining consistent fluid conditions can result in consistent and predictable heat transfer and expansion. This consistency allows manufacturing engineers and machinists to calibrate their machinery for consistent results.

Accordingly, described herein are systems that enable real-time multi-parameter monitoring of fluids in metal-working systems. In addition, described herein are fluorescence probes that enable in-line determination of fluid concentrations and/or soil loads. These fluorescence probes can be used in conjunction with real-time multi-parameter monitoring to provide accurate, useful, and relevant monitoring data to relevant personnel.

The disclosed devices and systems can be used to monitor fluid for metal-working processes including, for example and without limitation, grinding, turning, cutting, forming, broaching, tapping, cutting, honing, stamping, drawing, and drilling. It should be appreciated that the disclosed systems can be used with currently utilized cooling and/or lubricating fluids including, for example, soluble oils which consist of oil and an emulsifier and are typically between 10% and 90% water, synthetic fluid in which no oil is utilized, semi-synthetic fluids wherein some oil is utilized, water-miscible coolant, pure oil-based coolant, mineral oil, and the like. In some embodiments, the disclosed systems and methods are preferably used to monitor fluids that include oil-soluble coolant, semi-synthetic coolant, full synthetic coolant, and any drawing oil or stamping oil.

Example Metal-Working Installation with Real-Time Multi-Parameter Monitor

FIG. 1 illustrates an example metal-working installation 100 that includes metal-working equipment 102 having a fluid system 110 and a real-time, multi-parameter monitor or fluid monitoring system 120 for the fluid system 110. The fluid monitoring system 120 acquires measurements of characteristics of the fluid within the fluid system 110 and is configured to provide data indicative of characteristics of the fluid to one or more remote devices 162, 164, 166 in real time. The data can be delivered through a network 150 to the user devices 162, 164, 166 where a user 170 can monitor the state or well-being of the fluid system 110. This allows the user 170 to adjust operating parameters of the metal-working equipment 102 through a control system 130. In some embodiments, the fluid monitoring system 120 and the control system 130 communicate with the network 150 through a server 140, the server 140 being connected to the network 150. In certain embodiments, the fluid monitoring system 120 and/or the control system 130 are directly coupled to the network 150 for communication with the remote devices 162, 164, 166. In various implementations, the fluid monitoring system 120 and/or the control system 130 are coupled to the network 150 and to the server 140 to enable communication with the remote devices 162, 164, 166.

The metal-working equipment 102 includes any suitable machine or system typically used in the manufacturing sector and can include systems that involve the use of computers to control machine tools. Metal-working systems that can be controlled in this manner include lathes, grinders, milling machines, and all manner of equipment for cutting, forming, boring, milling, drilling and shaping of typically, though not exclusively, metal parts wherein the aforementioned processes are facilitated by application of cooling and/or lubricating fluids using the fluid system 110. A particular example of metal-working equipment is a CNC machining system where the CNC stands for computer numerical control. The metal-working equipment 102 includes workpieces and tools which cooperate to manufacture various and sundry metal parts.

The fluid system 110 is configured to provide metal-working fluid to the metal-working equipment 102. Typically, the metal-working fluid is a coolant and can be interchangeably referred to as a metal-working fluid or coolant throughout this disclosure. The fluid system 110 can include various components for storing and delivering fluid to the metal-working equipment 102. For example, coolant can be pumped from a reservoir to a part that is being machined in the metal-working equipment 102. The stream of coolant can be directed onto the part at the tool interface. The coolant can be used to sweep away metal turnings as the tool cuts into the part, to keep the tool and part at or near a targeted temperature, and/or to lubricate the tool and part. The coolant can be recirculated by continually directing the flow of the coolant to the tool interface and allowing the coolant to fall back into the reservoir. For example, the coolant can be delivered to the metal-working equipment 102 from the fluid system 110 through an inlet conduit or other fluid interface 106. Coolant that has been used can be returned to the fluid system 110 through an outlet conduit or other fluid interface 104.

The fluid monitoring system 120 is configured to monitor the fluids within the fluid system 110. The fluid monitoring system 120 includes a plurality of probes or sensors that are configured to measure and to calculate fluidic parameters associated with the operation of the metal-working equipment 102. The fluid monitoring system 120 can include sensors that measure pH, temperature, ORP, soil load, fluid concentration, and the like. The combination of parameters monitored by the fluid monitoring system 120 can provide an indication of the well-being of the fluid system 110 and/or the metal-working equipment 102 that is superior to any indication provided by or inferred from an individual parameter. The fluid monitoring system 120 is configured to generate data from measurements acquired with the plurality of sensors and to provide the data to the server 140 and/or to the remote devices 162, 164, 166 through the network 150. The fluid monitoring system 120 receives fluid to monitor from the fluid system 110 via an inlet conduit 114 or other fluid interface. After measurement, the fluid in the fluid monitoring system 120 is returned to the fluid system 110 through an outlet conduit 116 or other fluid interface. In some embodiments, the fluid monitoring system 120 is incorporated within the fluid system 110 so that fluid flowing or stored within the fluid system 110 is measured by the fluid monitoring system 120. In certain embodiments, the fluid monitoring system 120 includes a pump or other similar component configured to extract fluid from the fluid system 110 for measurement and to return the fluid after measurement to the fluid system 110.

The control system 130 can be configured to interface with the fluid system 110 and/or the metal-working equipment 102 to control aspects of the systems. For example, the control system 130 can control the fluid system 110 to adjust properties of the fluid being delivered to the metal-working equipment 102. As another example, the control system 130 can control the metal-working equipment 102 to adjust operating parameters such as ceasing operation or otherwise adjusting a rate of operation based on fluidic parameters measured by the fluid monitoring system 120. The control system 130 can include elements that provide automated control of these systems. For example, the control system 130 can control the metal-working equipment 102 and/or the fluid system 110 based on automatic control decisions based at least in part on data provided by the fluid monitoring system 120. In some embodiments, the control system 130 can receive commands from the user 170 through one of the remote devices 162, 164, 166, causing the control system 130 to alter operation of the metal-working equipment 102 and/or the fluid system 110. In various implementations, the control system 130 includes a combination of automated control decisions and commands based on user input. In addition, the control system 130 can be configured to generate alarms, notifications, or the like that are delivered to one or more remote devices 162, 164, 166.

Thus, due to the real-time multi-parameter data being provided by the fluid monitoring system 120 through the network 150, off-site personnel can remotely monitor the metal-working equipment 102 and the fluid system 110 and can adjust operational parameters from that remote location. This enables agile responses to changing conditions without intervention of a human on-site to physically interact with the metal-working equipment 102. Operators at a remote location can monitor one or many remote sites and operating conditions or events occurring at the remote locations and receive data or information in real time regarding operational parameters of the various systems. Moreover, permanent records of various fluid characteristics may be created and stored on the server 140 or the fluid monitoring system 120. In some embodiments, a record of the corrective action taken in response to data collected may also be made.

In some embodiments, the fluid system 110 includes supplies of one or more coolant or lubricant constituents that can be contained within storage tanks or vessels, for example. Concentrated coolants, lubricants, pH adjusters or any other fluid or constituent of a cooling and lubricating fluid which may be useful to provide, to augment, or to adjust the fluid characteristics can be part of the fluid system 110. The control system 130 can be configured to selectively adjust coolant parameters using such supplies.

It is to be understood that the metal-working installation 100 can include a plurality of metal-working equipment 102 with individual metal-working equipment 102 having respective fluid systems 110 and fluid monitoring systems 120. In such an installation 100, the plurality of metal-working equipment 102 and their associated subsystems (e.g., fluid system 110, fluid monitoring system 120, control system 130, etc.) can be configured to communicate with the server 140. Accordingly, the server 140 can receive and store data from the plurality of metal-working equipment 102. Similarly, the server 140 can transmit data through the network 150 to the remote devices 162, 164, 166 wherein the data can be from any metal-working equipment in communication with the server 140. Thus, the user 170 can monitor many metal-working equipment in a given installation (e.g., machine shop, manufacturing plant, or the like). Furthermore, multiple installations can be monitored in this way giving the user access to data from metal-working equipment at a plurality of installations at various geographic locations.

Example Real-Time, Multi-Parameter Fluid Monitoring Systems

Figure 2:
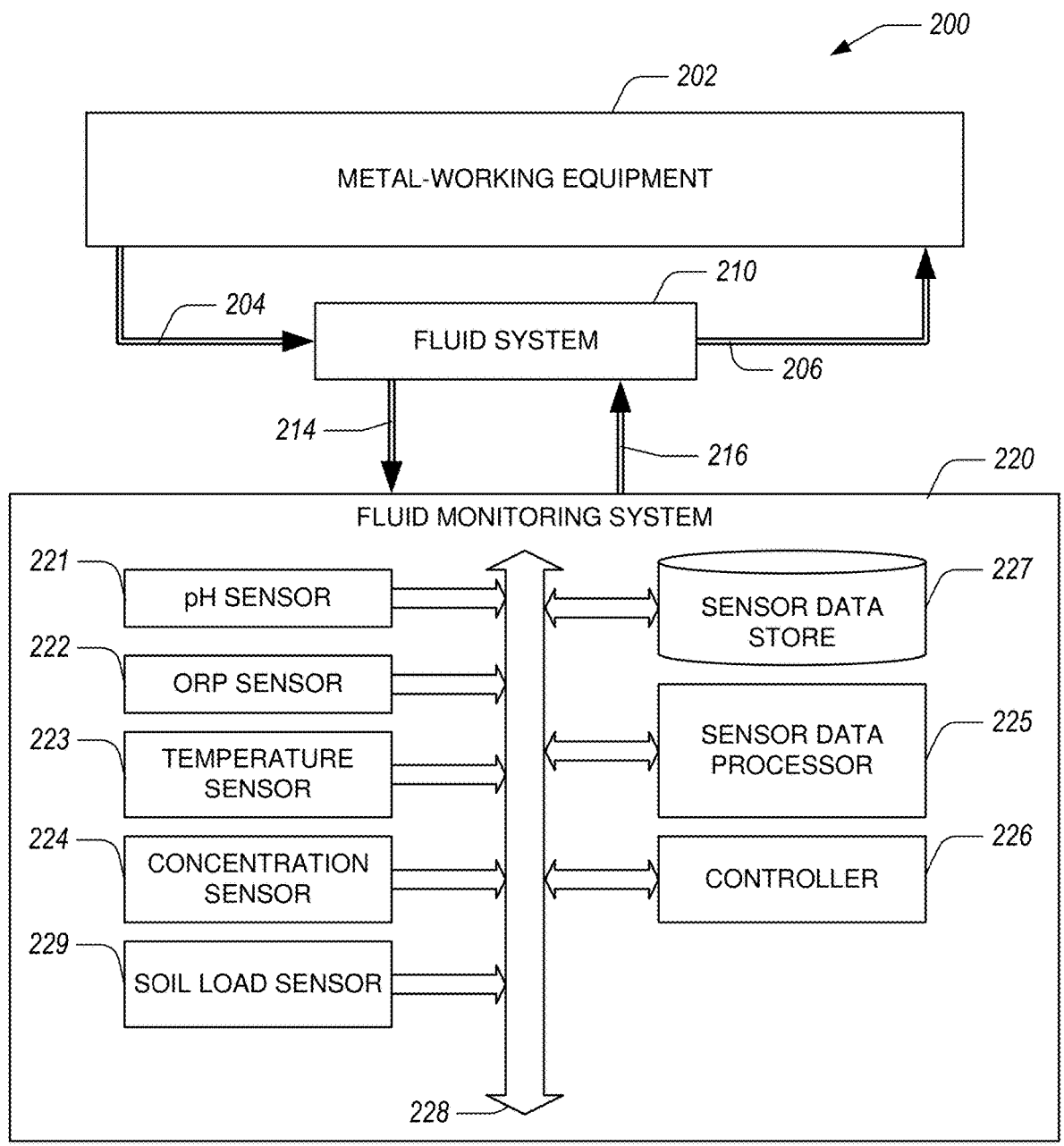
FIG. 2 illustrates an example of a multi-parameter fluid monitoring system that measures and determines parameters indicative of fluid quality in a metal-working system.

FIG. 2 illustrates an example of a multi-parameter fluid monitoring system 220 that measures and determines parameters indicative of fluid quality in metal-working equipment 202. A metal-working installation 200 includes the metal-working equipment 202, the fluid system 210, and the fluid monitoring system 220, similar to the metal-working installation 100 and respective components described herein with reference to FIG. 1. Accordingly, common elements and features of these components will not be described here again.

The fluid system 210 is configured to circulate fluid through the metal-working equipment 202 through conduits 204 and 206 (i.e., inlet conduit 204 and outlet conduit 206). Similarly, the fluid system is configured to circulate at least a portion of the fluid to the fluid monitoring system 220 through conduits 214 and 216 (i.e., inlet conduit 214 and outlet conduit 216). It should be understood, however, that the disclosed fluid monitoring system 220 can be configured for use in recirculated systems or other types of fluid installations. In such systems, the conduits 214, 216 may not be present or required.

The fluid monitoring system 220 can include hardware, software, and/or firmware components used to control sensors, to receive measurements, to determine fluidic parameters, and to transmit information to other components of the metal-working installation 200. The fluid monitoring system 220 can be configured to receive information from various sensors, to calculate one or more fluidic parameters based at least in part on the received information, and to communicate the calculated parameters to one or more systems such as the fluid system 210 (or a control system coupled to the fluid system 210 and/or the metal-working equipment 202). The fluid monitoring system 220 can include a pH sensor 221, an ORP sensor 222, a temperature sensor 223, a concentration sensor 224, a soil load sensor 229, a sensor data processor 225, a controller 226, and sensor data storage 227. Components of the fluid monitoring system 220 can communicate with one another, with external systems, and with other components of the metal-working installation 200 using communication bus 228. The fluid monitoring system 220 can employ any method described herein for measuring fluidic parameters, such as the example method 1000 described herein with reference to FIG. 10. Similarly, the fluid monitoring system 220 can include any suitable sensor for determining corresponding fluidic parameters such as the fluorescence probes described herein with reference to FIGS. 4A, 4B, 5A, and 5B.

The fluid monitoring system 220 includes the pH sensor 221. The pH sensor 221 includes a probe and associated electronics configured to measure the pH level of the fluid provided to the fluid monitoring system 220. The pH sensor 221 can include any suitable sensor or probe configured to measure pH level of the fluid. The measured pH (e.g., a measure of the acidity or alkalinity of the liquid) is an important factor in managing metal-working fluids. When bacteria levels become too high, the bacteria create an acidic byproduct, causing the pH to drop. When the pH falls to a level in which the fluid becomes mild to moderately acidic, the coolant becomes corrosive to ferrous metals, causing rust and corrosion of the work piece, tool holders, and other machine surfaces. When the pH becomes too high, it is typically the result of cross contamination by high alkaline chemicals. When the pH of a fluid is too high, it attacks non-ferrous metals, causing corrosion, pitting, and staining. Additionally, high pH levels are harsh on human skin tissue, causing irritation, including dermatitis.

The fluid monitoring system 220 includes an ORP sensor 222. The ORP sensor 222 includes a probe and associated electronics configured to measure the ORP of the fluid provided to the fluid monitoring system 220. The measured ORP is an indication of a fluid's capacity to either release or accept electrons from chemical reactions. Similar to pH, ORP values help to determine fluid quality. However, unlike pH, ORP values are affected by all oxidizing and reducing agents, not just acids and bases that influence pH measurement. Typical ORP sensors work in a fashion that is similar to a standard pH sensor. For example, an ORP sensor can be a two-electrode system that makes a potentiometric measurement. The ORP electrode serves as an electron donor or electron acceptor and a reference electrode supplies a constant stable output for comparison. Electrical contact is made with the fluid using a saturated potassium chloride (KCl) solution or other suitable solution.

The fluid monitoring system 220 includes a temperature sensor 223. The temperature sensor 223 includes a probe and associated electronics configured to measure the temperature of the fluid provided to the fluid monitoring system 220. The measured temperature can be indicative of temperature in the metal-working equipment 202 and/or the fluid system 210. If the temperature is too high or outside of a targeted region, it may indicate that the metal-working equipment is running too hot and may need to be shut down for a period of time. It may also indicate that the coolant is not behaving as anticipated or desired.

The fluid monitoring system 220 includes a concentration sensor 224. The concentration sensor 224 includes a probe and associated electronics configured to measure the concentration of the fluid provided to the fluid monitoring system 220. The concentration probe can include any suitable sensor configured to measure fluid concentration including, for example and without limitation, conductivity sensors, refractometry, and/or fluorescence probes. Fluid concentration is indicative of components of the fluid. For example, fluid concentration can be a measure of the ratio of a coolant or other component fluid in the metal-working fluid delivered to the metal-working equipment. If the fluid concentration is outside of a targeted region it may indicate that there are contaminants or undesirable elements in the fluid. For example, tramp oil, also known in the art as "sump oil," is unwanted oil that is created as a byproduct of metal-working operations, typically originating as hydraulic fluids or lubricating oils that seep into the coolant mixture. This can reduce tool life due to contamination in metal-working fluids. Additionally, tramp oil is a primary food source for bacteria, causing foul odors, shortened sump life, and other bacteria-related concerns, as previously described.

The fluid monitoring system 220 includes a soil load sensor 229. The soil load sensor 229 includes a probe and associated electronics configured to measure the soil load of the fluid provided to the fluid monitoring system 220. The soil load probe can include any suitable sensor configured to measure soil load including, for example and without limitation, conductivity sensors, refractometry, and/or fluorescence probes. Soil load is indicative of contamination of the fluid. For example, soil load can be a measure of the build-up of unsaponifiable oils and greases and a wide variety of solid soils that become mixed with the metal-working fluid. If the soil load becomes too high, it may cause the metal-working fluid to lose some of its designed properties. The soil load measurement can indicate that there are contaminants or undesirable elements in the fluid. The soil load may be related to the fluid concentration as well. Increased soil load may result in increases chemical consumption because concentrated fluid is typically added to counter increases in soil load. If the soil load becomes too high, it may get to a point where the fluid acts as an incubator for bacteria causing foul odors, shortened sump life, and other bacteria-related concerns, as previously described.

In some embodiments, the concentration sensor 224 and/or the soil load sensor 229 is a fluorescence probe, examples of which are described herein with reference to FIGS. 4A, 4B, 5A, and 5B. For example, the concentration sensor 224 and/or the soil load sensor 229 can be configured to generate light in a first wavelength (e.g., an excitation wavelength) and to measure emitted light and a second wavelength (e.g., an emission wavelength), the emitted light coming from a surface of the fluid in the fluid monitoring system 220. The measured emitted light can be used to determine fluid concentration and/or the soil load. Where the fluid monitoring system 220 includes both a concentration sensor 224 and a soil load sensor 229 and both sensors use a fluorescence probe, each sensor can be configured to utilize different wavelengths or colors of light in both excitation and emission, as described in greater detail herein.

The fluid monitoring system includes a sensor data processor 225 that is configured to receive data from the sensors 221-224 and 229 and to determine one or more parameters indicative of the quality of the fluids. The sensor data processor 225 includes one or more software modules, hardware components, and/or firmware elements configured to receive sensor data and to generate calculated parameters including, for example and without limitation, pH, ORP, temperature, soil load, and fluid concentration. The sensor data processor 225 can include a computer processor, in application-specific integrated circuit (ASIC), field programmable gate array (FPGA), or other suitable microprocessor.

The fluid monitoring system 220 includes a controller 226. The controller 226 can be configured to control operation of the sensors 221-224 and 229 as well as the sensor data processor 225 and/or the sensor data store 227. The controller 226 can include any suitable microprocessor and other computing components configured to interface with the various sensors, processors, and data stores of the fluid monitoring system 220.

The fluid monitoring system 220 includes the sensor data store 227 configured to store sensor measurements, calibration constants, algorithms, executable instructions (e.g., instructions for the sensor data processor 225 and/or the controller 226), and the like. The sensor data store 227 can be any suitable data storage device including, for example and without limitation, random access memory, read-only memory, solid-state disks, hard drives, flash drives, bubble memory, and the like.

Figure 3:
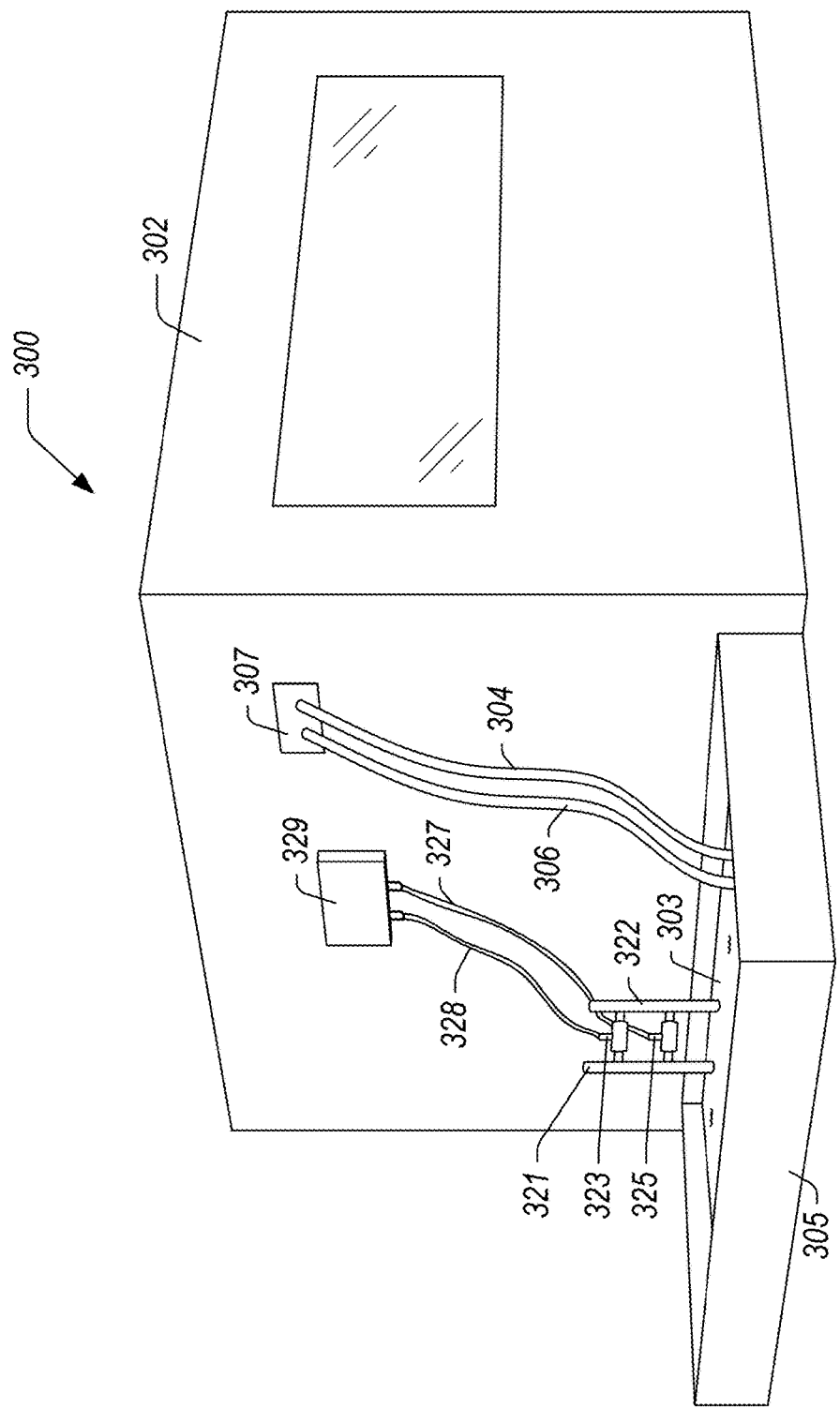
FIG. 3 illustrates an example computer numerical controlled ("CNC") machining system with a real-time, multi-parameter fluid monitor.

FIG. 3 illustrates an example computer numerical controlled ("CNC") machining system 302 in a metal-working installation 300. The machining system 302 includes a real-time, multi-parameter fluid monitoring system having a plurality of probes 323, 325. The machining system 302 can be any suitable metal-working equipment, such as the metal-working equipment 102 described herein with reference to FIG. 1. Accordingly, common elements and features of these components will not be described here again.

The machining system 302 includes a fluid system that is configured to circulate a coolant 303 to the machining system 302. The fluid system includes a fluid interface 307 having a fluid inlet 304 and a fluid outlet 306 that are in fluid communication with a sump 305. The coolant 303 are stored in the sump 305 and are supplied to the machining system 302 under pressure by a pump (not shown) in the fluid inlet 304. The fluid outlet 306 provides the coolant 303 to the sump 305.

The machining system 302 includes a fluid monitoring system that is configured to circulate at least a portion of the coolant 303 through the plurality of probes 323, 325. A supply line 321 provides at least a portion of the coolant 303 to a first probe 323 and to a second probe 325. A return line 322 returns the coolant 303 that passes through the plurality of probes 323, 325 to the sump 305. To move the coolant 303 through the fluid monitoring system, a pump (not shown) can be included as part of the supply line 321 and/or the return line 322.

The first probe 323 can include one or more of a pH sensor and an ORP sensor, examples of which are described herein with reference to FIG. 2. The second probe 325 can include one or more of a concentration sensor, a temperature sensor, and a soil load sensor, examples of which are described herein with reference to FIGS. 2, 4A, 4B, 5A, and 5B. The first probe 323 can receive power from a computer box 329 through electrical line 328. Similarly, the first probe 323 can communicate with the computer box 329 through the electrical line 328. The second probe 325 can receive power from the computer box 329 through electrical line 327. Similarly, the second probe 325 can communicate with the computer box 329 to the electrical line 327. In some embodiments, the first probe 323 and/or the second probe 325 communicate with the computer box 329 using wireless communication protocols (e.g., BLUETOOTH). In certain embodiments, the first probe 323 and/or the second probe 325 can be powered using battery power rather than power provided by the computer box 329. Accordingly, the first probe 323 and/or the second probe 323 can be installed without the use of any wired connections for communication or power.

The second probe 325 can include a concentration sensor and/or a soil load sensor. The concentration sensor and/or a soil load sensor can be an in-line refractometer, a sensor based on conductivity measurements, or a fluorescence probe. The fluorescence probe can be a sensor as described herein with reference to FIGS. 4A, 4B, 5A and 5B. As described herein with reference to FIGS. 5A and 5B, some embodiments of the second probe 325 can include a single fluorescence probe device that is configured to measure both fluid concentration and soil load. In some embodiments, the second probe 325 includes a first fluorescence probe configured to measure fluid concentration and a second fluorescence probe configured to measure soil load. Other configurations are possible as well. For example, the second probe 325 can include a fluorescence probe configured to measure soil load and a refractometer configured to measure concentration or vice versa.

Example in-Line Fluorescence Probes for Measuring Fluid Concentration

FIGS. 4A and 4B illustrate example fluorescence probes 400 configured to determine concentrations and/or soil loads of a fluid in metal-working equipment. In some embodiments, the fluorescence probe 400 can be configured to determine the metal-working fluid concentration and/or soil load in real time by directly measuring the native fluorescence of the metal-working fluid. In some embodiments, the fluorescence probe 400 can be configured to determine the metal-working fluid concentration and/or soil load in real time by measuring the fluorescence of one or more fluorescent tracers added to the metal-working fluid. In some embodiments, the fluorescence probe 400 can include an embedded programmable processor that can receive measured signals, process the signals, and determine the concentration and/or soil load. In certain embodiments, the fluorescence probe 400 is configured to send the measured signals to another component or system to determine the concentration and/or soil load. Accordingly, the fluorescence probe 400 can include one or more components configured for electronic communication with other systems either through wired or wireless communication methods.

As described herein, metal-working fluids contain natural, synthetic, or semi-synthetic oil. The oil components are dispersed in the aqueous metal-working fluid. The virgin metal-working fluid can be translucent and almost optically clear. As the metal-working fluid is blended with water and recirculated through the working machine system, it progressively becomes cloudy. This cloudiness makes many optical based measurement methods unsuitable for the defemination of the metal-working fluid concentration.

Traditionally, the concentration and/or soil load of the metal-working fluid is analyzed using a refractometer. A shortcoming of the inline refractometer is that if the optical window of the refractometer is not clean the quality and/or accuracy of the measurement can be compromised.

The disclosed fluorescence probe 400 or fluorometer is configured to measure the native fluorescence and/or fluorescence of a tracer to determine the concentration and/or soil load of the metal-working fluid. Furthermore, the disclosed fluorescence probe 400 measures the fluorescent light emitted from the surface of the fluid at an interface of an optical window 414.

The fluorescence probe 400 includes a flow-cell 415 having an inlet 411 and an outlet 419. In some embodiments, the flow-cell 415 can comprise a quartz tube. The probe 400 can be dipped into a reservoir of a metal-working fluid recirculation system or inserted into a flow path of a fluidic circuit. In either installation, the metal-working fluid (sample) fills the quartz tube.

The fluorescence probe 400 includes a fluorescent probe housing 410 that houses one or more optical components used in the fluorescence measurement. The fluorescent probe housing 410 includes an optical window 414 configured to interface with the fluid in the flow-cell 415.

Figure 5A:
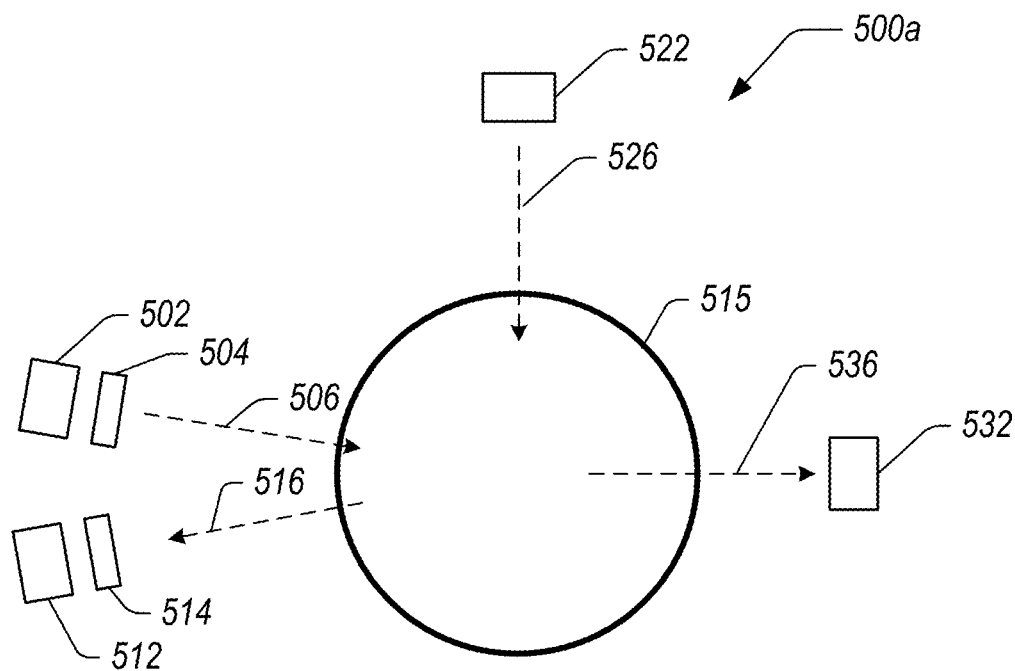
FIGS. 5A and 5B illustrate block diagrams of fluorescence probes that emit excitation light and measure emitted light to determine fluid concentrations and/or soil loads in metal-working systems.

FIG. 5A illustrates a block diagram of optical components in a first example fluorescence probe 500a, such as the fluorescence probe 400 of FIGS. 4A and 4B. The optical components are configured to emit excitation light and to measure emitted light to determine fluid concentrations or soil loads in metal-working equipment. The fluorescence probe 500a is configured to measure fluid concentration of a sample in a flow-cell 515. In some embodiments, the flow-cell 515 can have a diameter of about 6 mm. The flow-cell 515 can have a diameter that is at least 3 mm and/or less than or equal to 20 mm, at least 4 mm and/or less than or equal to 15 mm, or at least 5 mm and/or less than or equal to 10 mm.

The fluorescence probe 500a includes an excitation light source 502 and an excitation filter 504. The excitation light source 502 generates light having a first wavelength (e.g., in excitation wavelength) that is filtered by the excitation filter 504 and directed to the fluid within the flow-cell 515. The excitation light source 502 is aimed at the fluid making a small angle with respect to normal. In some embodiments, the small angle is less than or equal to 30°, is less than or equal to 25°, is less than or equal to 20°, is less than or equal to 15°, is less than or equal to 10°, or is less than or equal to 5°. The fluorescence probe 500 includes an emission light detector 512 and an emission filter 514. The emission light detector 512 is configured to detect emitted light that passes through the emission filter 514, the emitted light being emitted from a surface of the fluid. In some embodiments, the emitted light and the excitation light make a small angle with respect to each other. The excitation light source 502 can be any suitable light source including an LED. The emission light detector 512 can be any suitable light detector including a photodiode.

To measure concentration of the fluid in the flow-cell 515, excitation light 506 is directed to the fluid and emitted light 516 is detected by the emission light detector 512. The measured signal can be used to determine fluid concentration using a calibrated function that correlates measured emission light, transmitted excitation light, and fluid concentration. Similarly, the measured signal can be used to determine soil load using a calibrated function that correlates measured emission light, transmitted excitation light, and soil load.

The fluorescence probe 500a can include an auxiliary light source 522 configured to emit auxiliary light 526 directed to the fluid in the flow-cell 515. The fluorescence probe 500 can include an auxiliary photodiode 532 configured to detect scattered light from the auxiliary light source 522 and/or excitation light from the excitation light source 502. The scattered light 536 from the auxiliary light source 522 can be used to quantify turbidity of the sample. Detected excitation light at the auxiliary photodiode 532 can be used to measure the optical density of the sample. In some embodiments, the detected scattered light and/or the excitation light detected at the auxiliary photodiode 532 can be used to compensate for interference due to the sample color or scattering caused by the presence of particulate matter in the sample.

Figure 5B:
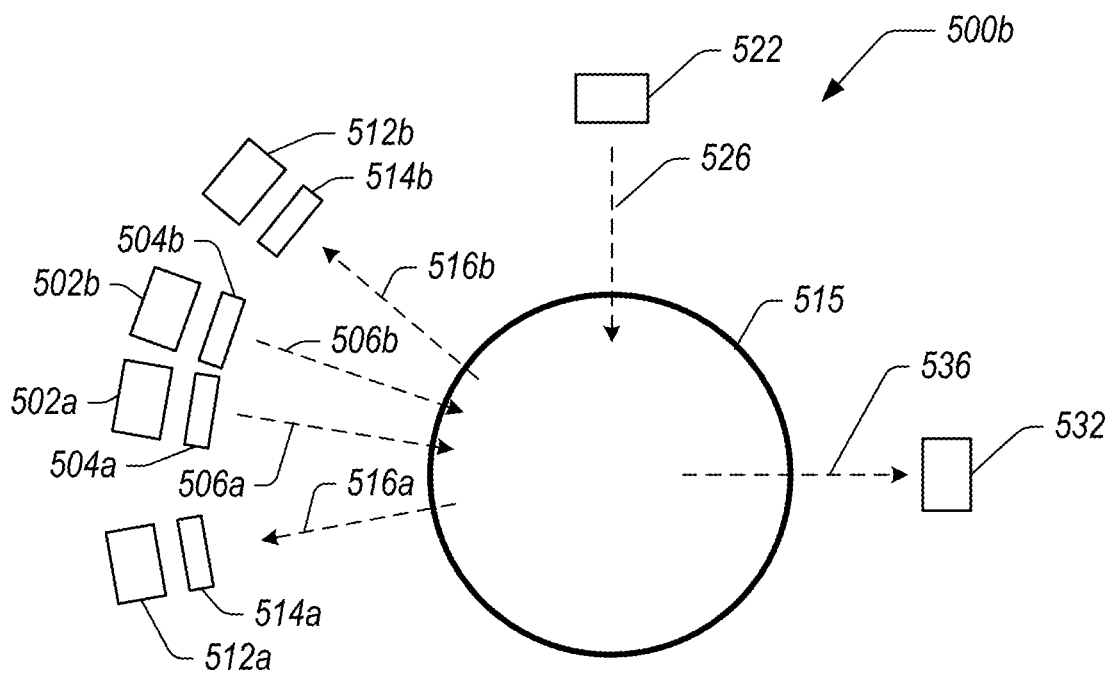

FIG. 5B illustrates a block diagram of optical components in a second example fluorescence probe 500b, such as the fluorescence probe 400 of FIGS. 4A and 4B. The fluorescence probe 500b is configured to acquire fluorescence measurements at two distinct wavelengths or colors. Advantageously, the fluorescence probe 500b can be configured to acquire measurements related to the fluid concentration and the soil load using a single probe.

The fluorescence probe 500b includes two sets of fluorescence measurement arrangements, each having an excitation light source 502a, 502b, an excitation filter 504a, 504b, an emission filter 514a, 514b, and an emission light detector 512a, 512b. The first fluorescence measurement arrangement includes the first excitation light source 502a, the first excitation filter 504a, the first emission filter 514a, and the first emission light detector 512a. The first fluorescence measurement arrangement is configured to emit first excitation light 506a having a first excitation color or wavelength that causes the fluid or a tracer in the fluid to fluoresce, emitting first emission light 516a at a first emission color or wavelength that is detected by the first fluorescence measurement arrangement. Similarly, the second fluorescence measurement arrangement includes the second excitation light source 502b, the second excitation filter 504b, the second emission filter 514b, and the second emission light detector 512b. The second fluorescence measurement arrangement is configured to emit second excitation light 506b having a second excitation color or wavelength that causes the fluid or a tracer in the fluid to fluoresce, emitting second emission light 516b at a second emission color or wavelength that is detected by the second fluorescence measurement arrangement.

In some embodiments, the fluorescence probe 500b can be embodied in a device such as the fluorescence probes illustrated in FIGS. 4A and 4B. In this way, a single fluorescence probe can be used to measure both fluid concentration and soil load. In certain embodiments, to measure both fluid concentration and soil load, two separate fluorescence probes are used. Each of these fluorescence probes can be embodied in devices such as the fluorescence probes illustrated in FIGS. 4A and 4B.

Figure 6:
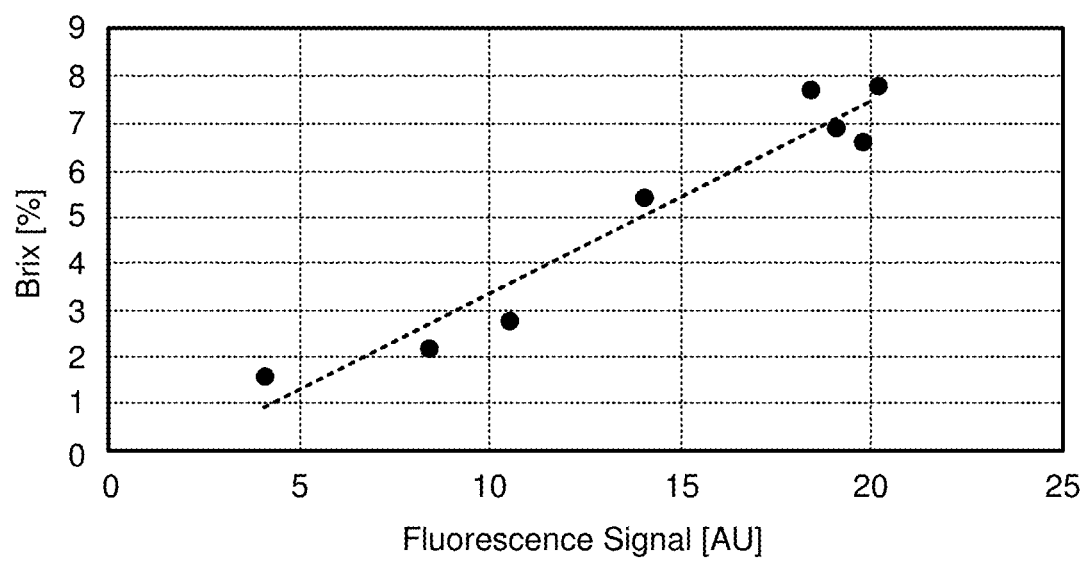
FIG. 6 illustrates a graph of measured fluorescence signals against brix concentrations determined using a refractometer.

FIG. 6 illustrates a graph of measured fluorescence signals against Brix concentrations determined using an offline refractometer. The Brix concentrations were determined by extracting a sample of the fluid measured by the fluorescence probe and manually determining the concentration using a refractometer. The relationship between the measured fluorescence signal may or not be linear, however, the concentration is a monotonic function of the measured fluorescence signal. Accordingly, a conversion from measured fluorescence signal to Brix concentration can be made, as illustrated by the graph in FIG. 6.

To further illustrate capabilities of the fluorescence probes described herein to measure fluid concentration, a fluorescence probe was installed in a CNC machining station along with a combined pH/ORP probe. An example of this configuration is illustrated in FIG. 3 wherein the fluorescence probe corresponds to the second probe 325 and the combined pH/ORP probe corresponds to the first probe 323. A sample was taken from the sump (e.g., sump 305) of the CNC metal-working fluid recirculation system using a beaker. The sample was diluted step-by-step by adding water to the beaker. The concentrations during the dilution were measured using a refractometer. FIG. 6 illustrates the comparison of the fluorescence signal with the measured Brix values.

Figure 7:
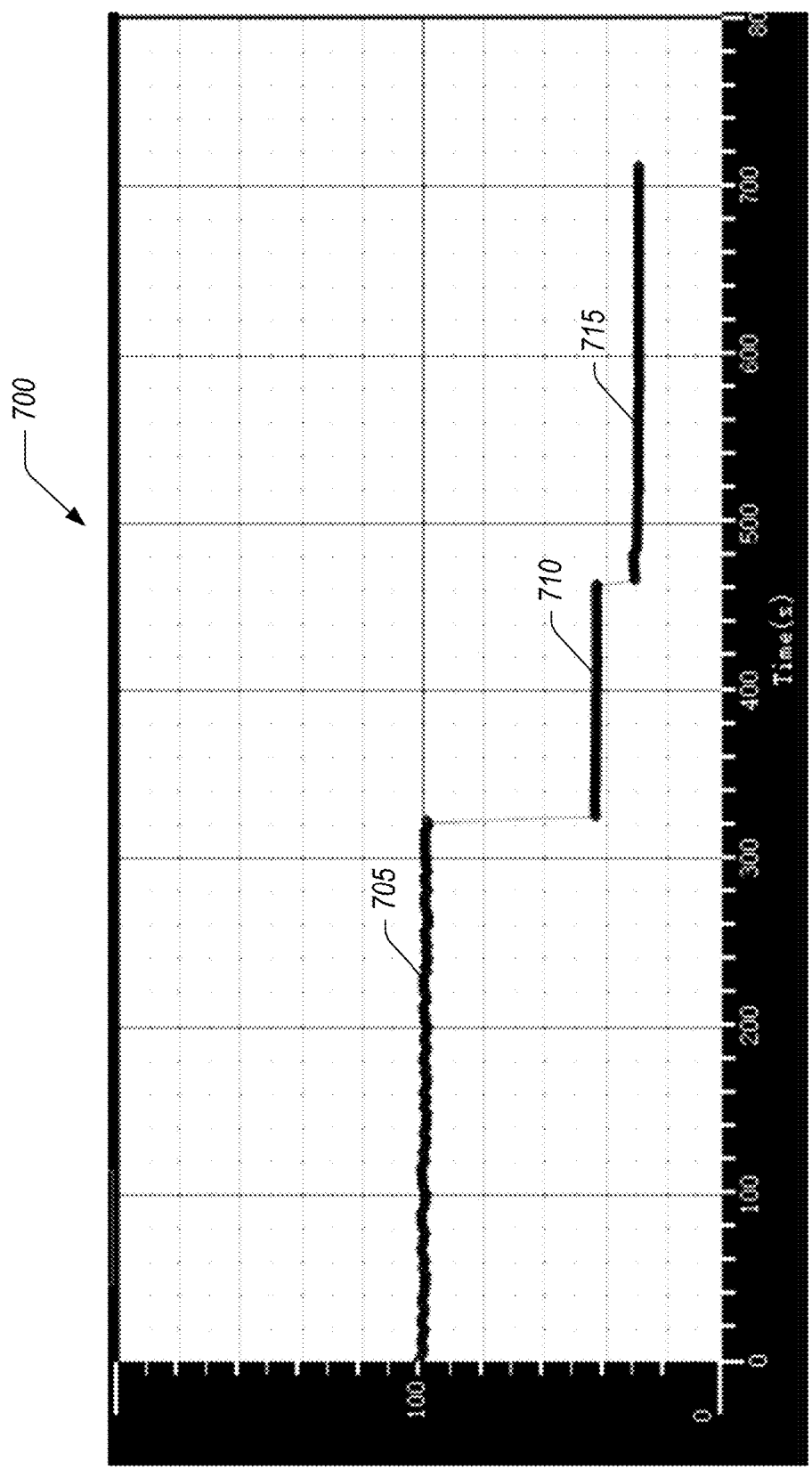
FIG. 7 illustrates a graph of measured fluorescence signal as a function of time with the concentration of fluid changing at certain times.

FIG. 7 illustrates a graph 700 of measured fluorescence signal as a function of time with the concentration of fluid changing at certain times. Portion 705 of the graph 700 corresponds to an undiluted metal-working fluid sample taken from a CNC machine. Portion 710 of the graph 700 corresponds to a 2/3 (sample/water) dilution. Portion 715 of the graph 700 corresponds to a 1/3 (sample/water) dilution. As can be seen in the graph 700, the fluorescence signal changes with changes in the fluid concentration.

Examples of Real-Time Graphical Monitoring

Figure 8:
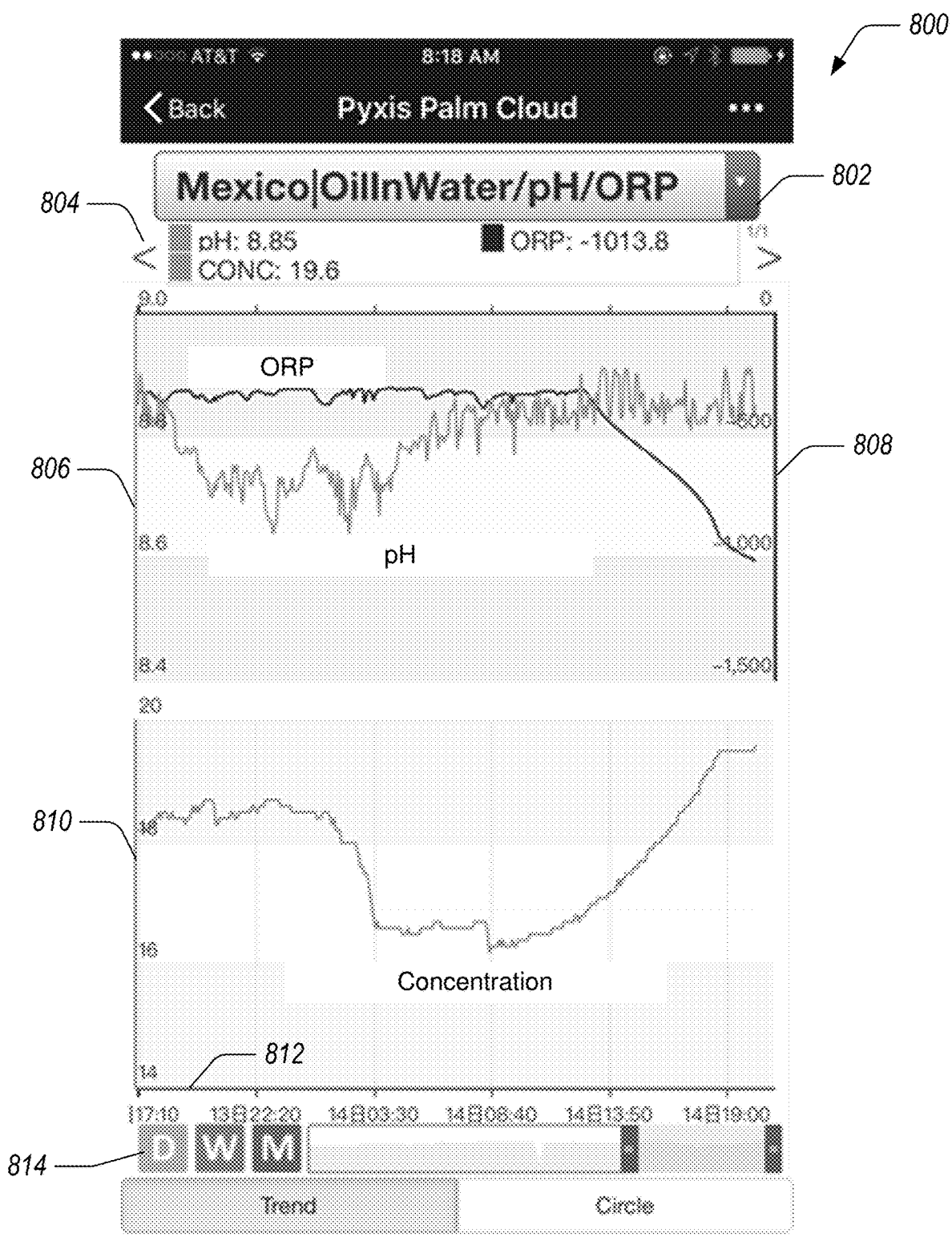
FIG. 8 illustrates a graphical user interface of a wireless device displaying real-time measurements and calculations of fluid parameters in a metal-working system that is remote from the wireless device.

FIG. 8 illustrates a graphical user interface 800 of a wireless device displaying real-time measurements and calculations of fluid parameters in metal-working equipment that is remote from the wireless device. As described herein with reference to FIG. 1, real-time monitoring parameters can be provided to a remote wireless device using the systems and methods described herein. The graphical user interface 800 illustrates that a remote device can be used to monitor fluidic parameters of remote metal-working equipment.

The graphical user interface 800 includes a system selection drop-down 802 that allows the user to select a desired location and/or metal-working equipment. The graphical user interface 800 also includes a legend 804 that also displays real-time measured values of various fluidic parameters. The graphical user interface 800 also includes a plurality of graphs configured to display real-time monitoring data as a function of time. The plurality of graphs can share a common x-axis that displays time. A first graph 806 has a first y-axis that displays pH values with a corresponding graph as a function of time. A second graph 808 displays ORP values as a function of time. A third graph 810 displays fluid concentration as a function of time. The graphical user interface 800 includes time window selection elements 814 labeled D, W, and M corresponding to day, week, and month time frames. The time window selection elements 814 can be configured to change the amount of time represented on the x-axis of the various graphs displayed in the graphical user interface 800.

The disclosed graphical user interface 800 allows off-site personnel to monitor the well-being and status of remote metal-working equipment. In some embodiments, the graphical user interface 800 can include control elements that allows the off-site personnel to adjust operating parameters of the remote metal-working equipment. The graphical user interface 800 can also include alarms and notifications to indicate when one or more parameters of metal-working equipment are outside of a targeted or designated range. This can allow off-site personnel to quickly assess whether one or more metal-working equipment are operating under dangerous or undesirable conditions.

Example Method of Monitoring Multiple Parameters in Real Time

Figure 9:
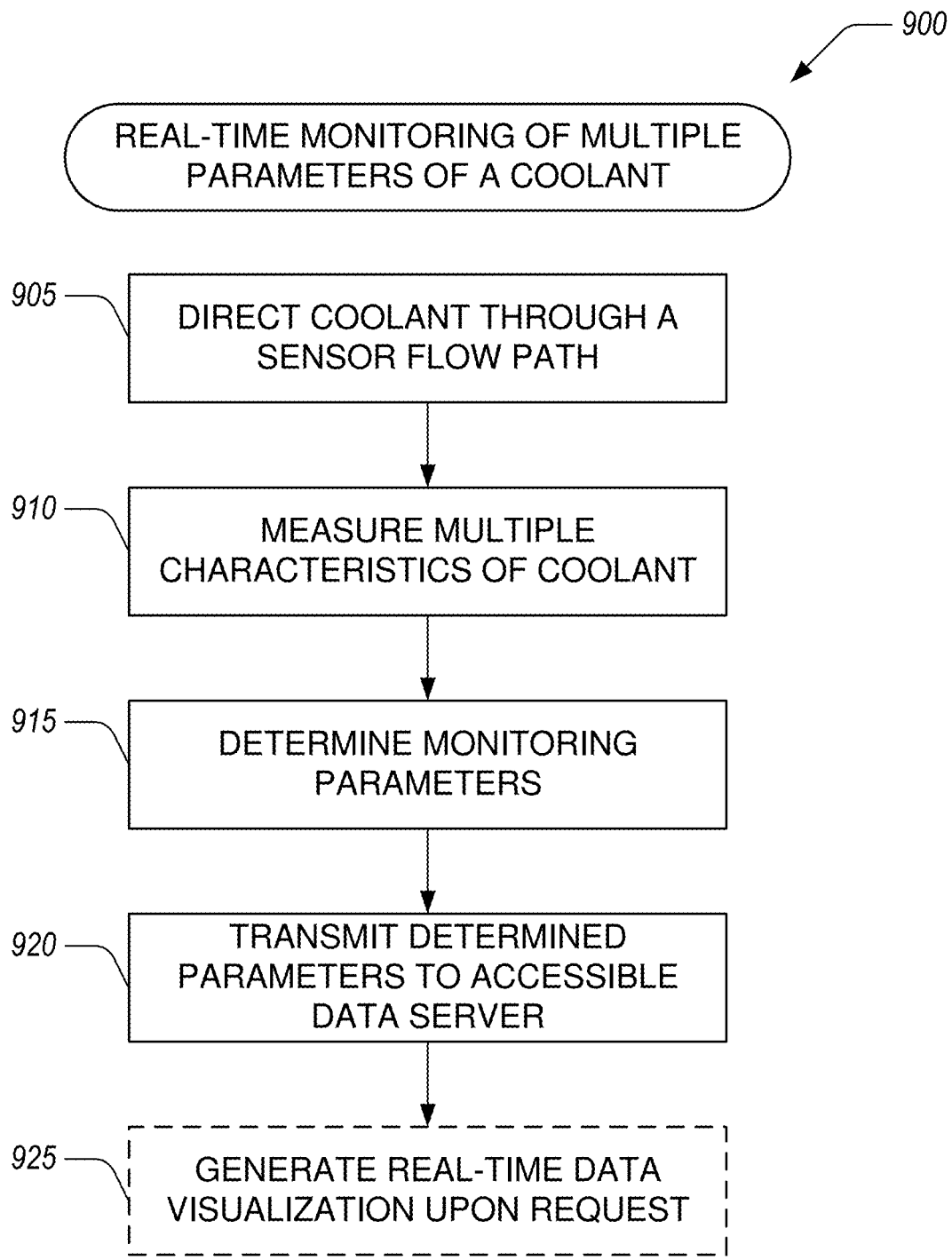
FIG. 9 illustrates a flowchart of an example method of monitoring in real time multiple parameters of a metal-working fluid of a metal-working system.

FIG. 9 illustrates a flowchart of an example method 900 of monitoring in real time multiple parameters of a metal-working fluid (e.g., a coolant) of metal-working equipment. The method 900 can be performed by the fluid monitoring systems described herein with reference to FIGS. 1, 2, and/or 3. In some embodiments, the method 900 can be performed by one or more components of the fluid monitoring system, wherein individual steps in the method 900 can be performed by a single component or a combination of components. Similarly, in some embodiments, individual steps in the method 900 can be performed by one or more systems including, for example, a fluid monitoring system, a fluid system, metal-working equipment, a control system, and/or a server.

In block 905, the fluid monitoring system directs coolant through a sensor flow path. The coolant can be directed through the sensor flow path using one or more pumps and one or more conduits. In some embodiments, the fluid monitoring system is part of the fluid system such that it measures coolant within the fluid system without requiring it to be redirected through a separate fluid monitoring system. For example, one or more sensors can be placed in a sump or in a fluidic circuit that provides coolant to metal-working equipment.

In block 910, the fluid monitoring system measures multiple characteristics of the coolant flowing through the sensor flow path. The characteristics can include conductivity, fluorescence from a surface of the fluid, resistance of the fluid, color of the fluid, optical absorptivity of the fluid, and the like. The measurements acquired by the fluid monitoring system include the raw data generated by associated sensors.

In block 915, the fluid monitoring system processes the measurements acquired in block 910 to determine associated fluidic parameters based at least in part on those measurements. The parameters can include, for example and without limitation, pH, temperature, ORP, soil load, and/or concentration. The fluid monitoring system is configured to measure a plurality of parameters associated with the well-being of the coolant in metal-working equipment to provide an improved indication of the well-being of the metal-working equipment.

In block 920, the fluid monitoring system transmits the parameters determined in block 915 to a server. The server can be accessible to one or more remote devices to allow remote monitoring of corresponding metal-working equipment. The server can restrict access to the data through one or more authentication and/or security configurations.

In optional block 925, the fluid monitoring system generates real-time data visualizations upon request. In some embodiments, the step is performed by a server or other device that has access to the data acquired by the fluid monitoring system. For example, a remote device may receive raw data from a server and generate the real-time data visualization requested. An example of such data visualization is provided in FIG. 8.

Example Method of Measuring Concentration Using Fluorescence

Figure 10:
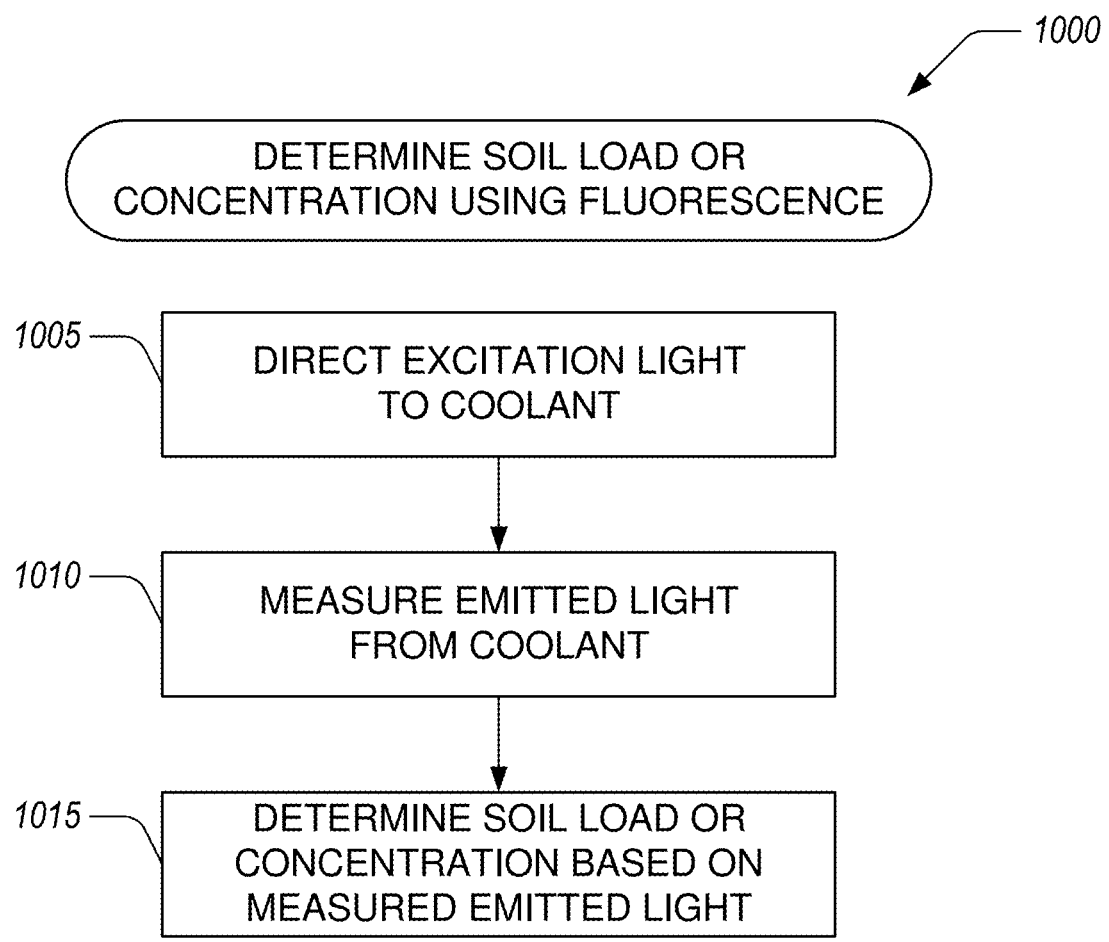
FIG. 10 illustrates a flowchart of an example method of determining fluid concentration and/or soil load of a metal-working system coolant using a fluorescence probe.

FIG. 10 illustrates a flowchart of an example method 1000 of determining fluid concentration and/or soil load of metal-working fluid (e.g., a coolant) using a fluorescence probe. The method 1000 can be performed by the fluorescence probes disclosed herein with reference to FIGS. 4A, 4B, 5A and 5B. In some embodiments, one or more portions of the method 1000 can be performed by a system such as the fluid monitoring systems described herein with reference to FIGS. 1, 2, and 3.

In block 1005, the fluorescence probe generates excitation light and directs the excitation light to coolant. The coolant can be flowing through a flow tube that is part of the fluorescence probe or the coolant can be in a coolant reservoir. In some embodiments, the excitation light is directed through a window to a surface of the coolant.

In block 1010, the fluorescence probe measures light emitted from a surface of the coolant. The emitted light can be referred to as emission light. The emitted light can have a different wavelength than the excitation light. Accordingly, the fluorescence probe measures light fluorescing from a surface of the coolant. In some embodiments, the emitted light and the excitation light form a relatively small angle with respect to each other. For example, the relative angle between the emitted light and the excitation light can be less than or equal to about 30 degrees, less than or equal to about 20 degrees, less than or equal to about 15 degrees, or less than or equal to about 10 degrees.

In block 1015, the fluorescence probe determines the concentration and/or the soil load based on the measured emitted light. In some embodiments, the measurements acquired with a light detector that detects the emitted light are provided to an external system that determines the concentration and/or the soil load. In some embodiments, the fluorescence probe and/or the external system include algorithms, calibration constants, and/or functions that translate measurement values to concentration and/or soil load values. In certain implementations, such algorithms, calibration constants and/or functions can be different for different coolants and/or metal-working equipment. For example, calibration can be made for different coolant compositions so that measured fluorescence signals can be accurately correlated with fluid concentrations and/or soil loads. In some embodiments, adjustments can be made to the conversion between measurement and concentration and/or soil load based on data acquired using off-line means such as refractometry. Accordingly, the method 1000 can be updated to improve the accuracy of the concentration and/or soil load measurements acquired by the fluorescence probe(s).

In some embodiments, the method 1000 is performed using the native fluorescence of the coolant. In some embodiments, the method 1000 is performed using a fluorescent tracer added to the coolant. The fluorescent tracer can be mixed with the coolant or a particular fluid component of the metal-working fluid.

In various embodiments, the method 1000 can be used to measure both concentration and soil load using fluorescence. In such embodiments, the concentration can be measured based on native fluorescence of the fluid while the soil load can be measured based on fluorescence of a tracer added to the fluid. Similarly, the soil load can be measured based on native fluorescence of the fluid while the concentration can be measured based on fluorescence of a tracer added to the fluid. In addition, the concentration can be measured based on fluorescence of a first tracer added to the fluid and the soil load can be measured based on fluorescence of a second tracer added to the fluid, where the colors of the tracers are distinct from one another.

Additional Embodiments

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional subcomponents to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Some aspects of the systems and methods described herein can advantageously be implemented using, for example, computer software, hardware, firmware, or any combination of computer software, hardware, and firmware. Computer software can comprise computer executable code stored in a computer readable medium (e.g., non-transitory computer readable medium) that, when executed, performs the functions described herein. In some embodiments, computer-executable code is executed by one or more general purpose computer processors. A skilled artisan will appreciate, in light of this disclosure, that any feature or function that can be implemented using software to be executed on a general purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

Multiple distributed computing devices can be substituted for any one computing device described herein. In such distributed embodiments, the functions of the one computing device are distributed (e.g., over a network) such that some functions are performed on each of the distributed computing devices.

Some embodiments may be described with reference to equations, algorithms, and/or flowchart illustrations. These methods may be implemented using computer program instructions executable on one or more computers. These methods may also be implemented as computer program products either separately, or as a component of an apparatus or system. In this regard, each equation, algorithm, block, or step of a flowchart, and combinations thereof, may be implemented by hardware, firmware, and/or software including one or more computer program instructions embodied in computer-readable program code logic. As will be appreciated, any such computer program instructions may be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, may be implemented by special purpose hardware-based computer systems which perform the specified functions or steps, or combinations of special purpose hardware and computer-readable program code logic means.

Furthermore, computer program instructions, such as embodied in computer-readable program code logic, may also be stored in a computer readable memory (e.g., a non-transitory computer readable medium) that can direct one or more computers or other programmable processing devices to function in a particular manner, such that the instructions stored in the computer-readable memory implement the function(s) specified in the block(s) of the flowchart(s). The computer program instructions may also be loaded onto one or more computers or other programmable computing devices to cause a series of operational steps to be performed on the one or more computers or other programmable computing devices to produce a computer-implemented process such that the instructions which execute on the computer or other programmable processing apparatus provide steps for implementing the functions specified in the equation(s), algorithm(s), and/or block(s) of the flowchart(s).

Some or all of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list. The word "exemplary" is used exclusively herein to mean "serving as an example, instance, or illustration." Any implementation described herein as "exemplary" is not necessarily to be construed as preferred or advantageous over other implementations.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method of monitoring a concentration of a metal-working fluid, the method comprising:
   directing first excitation light having a first excitation color to a surface of the metal-working fluid;
   measuring first fluorescent light having a first emission color emitted from the surface of the metal-working fluid, the first fluorescent light forming a small angle with respect to the first excitation light;
   directing second excitation light having a second excitation color different from the first excitation color to the surface of the metal-working fluid;
   measuring second fluorescent light having a second emission color different from the first emission color emitted from the surface of the metal-working fluid, the second fluorescent light forming a small angle with respect to the second excitation light;
   determining the concentration of the metal-working fluid based on the measured first fluorescent light; and
   determining the soil load of the metal-working fluid based on the measured second fluorescent light.

2. The method of claim 1 further comprising filtering the first excitation light prior to the first excitation light reaching the surface of the metal-working fluid.

3. The method of claim 2 further comprising filtering the first fluorescent light prior to measuring the first fluorescent light.

4. The method of claim 1 further comprising directing a portion of a metal-working fluid from a reservoir to a flow-cell.

5. The method of claim 1 further comprising determining a pH level, a temperature, and an oxidation reduction potential of the metal-working fluid based at least in part on measurements from one or more sensors.

6. The method of claim 5 further comprising transmitting the determined pH level, temperature, oxidation reduction potential, and fluid concentration or soil load to one or more remote devices.

7. The method of claim 6 further comprising generating a real-time data visualization based on the transmitted pH level, temperature, oxidation reduction potential, and fluid concentration or soil load.

8. The method of claim 1 further comprising automatically adjusting a property of the metal-working fluid in response to the determined concentration or soil load.

* * * * *